United States Patent [19]

Ronsen et al.

[11] Patent Number: 4,996,195

[45] Date of Patent: Feb. 26, 1991

[54] DERIVATIVES OF α,D-GLUCOFURANOSE OR α,D-ALLOFURANOSE AND INTERMEDIATES FOR PREPARING THESE DERIVATIVES

[75] Inventors: Bruce Ronsen, River Forest; Sudershan K. Arora, Westchester; Albert V. Thomas, Niles, all of Ill.

[73] Assignee: Greenwich Pharmaceuticals Inc., Ft. Washington, Pa.

[21] Appl. No.: 294,838

[22] Filed: Jan. 9, 1989

[51] Int. Cl.$^5$ ............................................. A61K 31/70
[52] U.S. Cl. .................................... 514/23; 514/25; 514/825; 514/861; 536/1.1; 536/4.1; 536/17.2; 536/17.5; 536/18.7; 536/54
[58] Field of Search ................... 514/23, 25, 825, 861; 536/1.1, 4.1, 17.2, 17.5, 18.7, 54

[56] References Cited

U.S. PATENT DOCUMENTS

| | | | |
|---|---|---|---|
| Re. 30,354 | 7/1980 | Gordon | 536/4.1 |
| Re. 30,379 | 8/1980 | Gordon | 536/4.1 |
| Re. 32,268 | 10/1986 | Gordon | 514/25 |
| 2,461,478 | 2/1949 | Kaszuba | 106/135 |
| 2,875,194 | 2/1959 | Baker et al. | 536/17.3 |
| 2,960,452 | 11/1960 | Slager et al. | 549/361 |
| 3,586,664 | 6/1971 | Kohno et al. | 536/4.1 |
| 3,832,355 | 8/1974 | Jaffe et al. | 549/361 |
| 3,939,145 | 2/1976 | Gordon | 536/17.9 |
| 3,939,146 | 2/1976 | Gordon | 514/25 |
| 3,965,262 | 6/1976 | Gordon | 514/53 |
| 4,010,275 | 3/1977 | Wilhelmi | 514/23 |
| 4,016,261 | 4/1977 | Gordon | 536/120 |
| 4,017,608 | 4/1977 | Gordon | 536/120 |
| 4,032,650 | 6/1977 | Molle et al. | 514/470 |
| 4,056,322 | 11/1977 | Gordon et al. | 536/4.1 |
| 4,220,782 | 9/1980 | Stoltefuss | 536/4.1 |
| 4,251,520 | 2/1981 | Bruzzese et al. | 536/4.1 |
| 4,554,349 | 11/1985 | Ponpipom et al. | 536/55 |
| 4,735,934 | 4/1988 | Gordon | 514/825 |
| 4,738,953 | 4/1988 | Gordon | 514/25 |

Primary Examiner—Ronald W. Griffin
Attorney, Agent, or Firm—Finnegan, Henderson, Farabow, Garrett & Dunner

[57] ABSTRACT

Derivatives of -α,D-glucofuranose α,D-allanfuranose and intermediates for preparing these derivatives are described. These derivatives are useful for treating animals and mammals with inflammatory and/or autoimmune disorders such as psoriasis, atopic dermatitis, rheumatoid arthritis, osterarthritis, scleroderma and systemic lupus erythematosus.

32 Claims, No Drawings

DERIVATIVES OF α,D-GLUCOFURANOSE OR α,D-ALLOFURANOSE AND INTERMEDIATES FOR PREPARING THESE DERIVATIVES

BACKGROUND OF THE INVENTION

1. Field of the Invention

This invention relates to derivatives of α,D-glucofuranose and α, D-allofuranose compounds and intermediates for preparing these derivatives. More particularly, this invention relates to 1,2 and 1,2:3,5-O-isopropylidene-α,D-glucofuranose derivatives or α,D-allofuranose. The derivatives of this invention are useful for treating animals and mammals with inflammatory and/or autoimmune disorders such as psoriasis, atopic dermatitis, rheumatoid arthritis, osteoarthritis, scleroderma and systemic lupus erythematosus.

2. Description of the Related Art

Blocked acetals of hexoses exist as solids or liquids at room temperature. Various blocking methods are described in U.S. Pat. Nos. 2,715,121 and 4,056,322, the disclosures of which are incorporated by reference herein in their entireties. For example, in instances where an aldehyde or ketone is reacted with the hydroxyl groups on adjacent or neighboring sugar carbon atoms, the hexose may be blocked in a plurality of positions, such as, e.g., the 1,2- and/or 5,6- positions. In the 1,2:5,6-blocked hexoses the ring forms between carbons 1 and 4, leaving carbon 3 free to etherize; in the 1,2:3,5-blocked hexoses, the ring forms between carbons 1 and 4, leaving carbon 6 free to etherize; and in 1,2:4,6-blocked hexoses, the ring forms between carbons 1 and 2, again leaving carbon 3 free to etherize. Thus, 1,2:5,6-blocked hexoses may form 3-0 ethers, 1,2:3,5-blocked hexoses may form 6-O ethers, and 1,2:4,6-blocked hexoses may also form 3-0 ethers After the desired blocking of the monosaccharide is obtained, the unblocked position of the monosaccharide can be etherized. Ethereal substituted hexose monosaccharides, such as 1,2:5,6-Di-O-isopropylidene 3-0-3('N',N'-dimethylamino-n-propyl)-α,D-glucofuranose (i.e. THERAFECTIN®), amiprilose hydrochloride are known and have demonstrated utility in managing the signs and symptoms of rheumatoid arthritis. These compounds have activity more generally as immunomodulators, and therefore have a therapeutic effect on other autoimmune disorders such as psoriasis, eczema or lupus.

For certain indications, high doses of these monosaccharides, such as THERAFECTIN®, are needed to produce effective results. These compound, however, can be topically applied. It is therefore an object of the present invention to provide an α,D-glucofuranose or α,D-allofuranose compound that exhibits greater potency than THERAFECTIN® when orally administered.

With respect to 1,2:3,5-Di-O-isopropylidene,-α,D-glucofuranose, the literature discloses its formation in trace to small quantities as a by-product of chemistries using glucose, acetone or other carbohydrates, (D. C. C. Smith, Journal of Chemical Society, 1956, 1244-1247). This compound is, however, prepared in poor yield and with a difficult work up from classical organic chemical reactions as described elsewhere in the literature.

It is therefore also an object of the present invention to provide a simple and efficient process for preparing 1,2:3,5-Di-O-isopropylidene-α,D-glucofuranose.

Additional objects and advantages of the invention will be set forth in the description which follows, and in part will be apparent from the description, or may be learned by practice of the invention. The objects and advantages of the invention may be realized and obtained by means of the mechanisms and combinations pointed out in the appended claims.

SUMMARY OF THE INVENTION

To achieve the foregoing objects, and in accordance with the purposes of the invention as embodied and broadly described herein, there is provided a monosaccharide compound selected from the group consisting of:

1,2:3,5-Di-O-isopropylidene-6-deoxy-6-thio-3'(N',N'-dimethylamino-n-propyl)-α,D-glucofuranose;

1,2-O-isopropylidene-3-O-n-heptyl-α,D-glucofuranose;

1,2-O-isopropylidene-3-deoxy-3-amino-3'-(propan-1'-ol)-α,D-allofuranose; and 1,2:3,5-Di-O-isopropylidene-6-O-2'(N'-ethylpyrrolidyl)-α,D-glucofuranose.

The present invention also provides a pharmaceutical composition for the treatment of inflammatory and/or autoimmune disorders. The composition comprises an effective amount of at least one of these monosaccharide compounds or a physiologically acceptable acid-addition salt thereof with a pharmaceutically acceptable carrier.

These compounds have demonstrated in vitro decreased skin cell proliferation and inhibition of the proliferative response of splenic T-lymphocytes to known mitogens. T-lymphocytes are the immune cells that regulate immune responses. Therefore, it is believed that the present monosaccharides can be used for treating animals and humans with inflammatory and/or autoimmune disorders such as psoriasis, atopic dermatitis, rheumatoid arthritis, ostearthritis, scleroderma and systemic lupus erythematosus.

Advantageously, the compounds of the present invention exhibit greater potency in terms of their activity than the monosaccharides such as THERAFECTIN®. Therefore, the present compounds can be administered internally as well as externally.

The present invention is also directed to a process for preparing 1,2:3,5-Di-O-isopropylidene-α,D-glucofuranose which can be used as a precursor in preparing the compounds of this invention. This process comprises adding 1,2-O-isopropylidene-α,D-glucofuranose to a solvent such as di-haloalkyl and a non-reactive organic base such as pyridine, triethylamine, or the like. The resultant mixture is contacted with trimethylacetyl chloride to form a 6-O-trimethylacetate ester or 1,2-O-isopropylidene- α,D-glucofuranose. The trimethylacetate ester is dissolved in 2,2-dimethyoxypropane in the presence of a catalytic amount of p-toulene sulfonic acid. The trimethylacetate ester is then removed by adding excess amounts of sodium hydroxide in aqueous solution or an aqueous ethanolic solution at reflux temperature.

DETAILED DESCRIPTION OF THE INVENTION

The compounds of the present invention include the following monosaccharides:

1,2:3,5-Di-O-isopropylidene-6-deoxy-6-thio-3'(N',N'-dimethylamino-n-propyl)-α,D-glucofuranose (Empirical formula $C_{17}H_{31}NO_5S$) having the following structural formula;

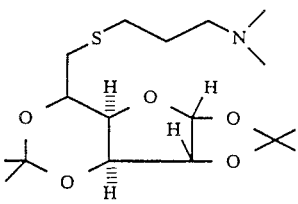

1,2-O-isopropylidene-3-O-n-heptyl-α,D-glucofuranose (Empirical formula $C_{16}H_{30}NO_6$) having the following structural formula;

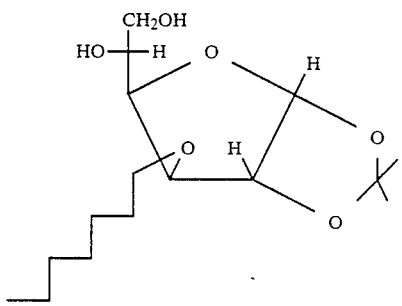

1,2-O-isopropylidene-3-deoxy-3-amino-3'-(propan-1'-ol) α,D-allofuranose (Empirical formula $C_{12}H_{23}NO_6$) having the following structural formula;

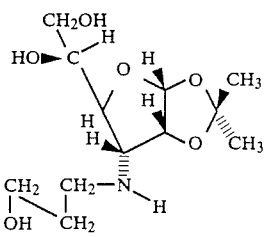

1,2:3,5-Di-O-isopropylidene-6-O-2'(N'-ethylpyrrolidyl)-α,D-glucofuranose (Empirical formula $C_{16}H_{31}NO_6$) having the following structural formula;

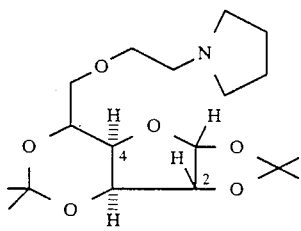

A simple and efficient process for the preparation of 1,2:3,5-Di-O-isopropylidene-α,D-glucofuranose is described herein which starts with 1,2-O-isopropylidene-α,D-glucofuranose The art of this synthesis is the ability to control the esterification of the 6-hydroxyl residue with trimethylacetyl chloride. Two other secondary hydroxyl residues are present in this starting material at positions 3 and 5 and normally react equally well with the esterifying reagent, trimethylacetyl chloride. In fact, attempts have been made using reagents such as acetic anhydride, benzoyl chloride, other hindered acid chlorides, hindered salicylic acid chlorides, or sulfonyl chlorides to find an esterfying agent which reacts primarily at the 6-hydroxyl residue. However, these reagents do not exclusively react with the terminal 6-hydroxyl residue when combined under standard conditions or controlled conditions or do not react at all.

To a solution of 1,2-O-isopropylidene-α,D-glucofuranose in a di-haloalkyl, preferably dry methylene chloride, pyridine is added, preferably dry pyridine. Subsequently, trimethylacetyl chloride is added dropwise while stirring at room temperature until it is all added. By this process the trimethylacetate ester readily forms at the 6-position to form 1,2-O-isopropylidene-α,D-glucofuranose-6-O-trimethylacetate ester. The ester is isolated as a white crystalline powder.

The second step in the sequence after the formation and purification of the 6-O-trimethylacetate ester of 1,2-O-isopropylidene-α,D-glucofuranose is the addition of an acetone equivalent to the dihydroxyl residues at the 3 and 5 positions of the glucofuranose moiety. This addition is accomplished efficiently by dissolving the intermediate compound, 6-O-trimethylacetate ester of 1,2-O-isopropylidene-α,D-glucofuranose, in 2,2-dimethyoxypropane containing catalytic amounts of p-toluene sulfonic acid preferably using the conditions described in Example 2 herein, a reaction occurs rapidly and the product is isolated in nearly quantitative yields.

The product, 6-O-trimethylacetate ester of 1,2:3,5-Di-O-isopropylidene-α,D-glucofuranose is a clear viscous liquid at room temperature. Removal of the trimethylacetate ester from the 6-position by saponification is completed in quantitative amounts when using excess amounts of sodium hydroxide in aqueous solutions or aqueous ethanolic solutions at reflux temperature. The 1,2:3,5-Di-O-isopropylidene-α,D-glucofuranose so formed is stable and exists as a clear colorless syrup at room temperature and solidifies to a white crystalline powder on standing.

It is noted that while acetone equivalents such as 2,2 dimethoxypropane are preferred as the blocking groups, other blocking groups may be selected so long as the particular blocking substituent does not interfere with the synthesis process, as can be routinely determined by one of ordinary skill in the art.

An alkyl ether from 1,2:3,5-Di-O-isopropylidene-α,D-glucofuranose is made with a solid phase Williamson synthesis as disclosed in U.S. patent application Ser. No. 07/203,884 (filed June 8, 1988) by reacting the glucofuranose with dry powdered sodium hydroxide flakes using the reaction conditions described in Examples 4 through 8 herein. The ether so formed occurs exclusively at the 6-position with purity in excess of 99% and yields in excess of 80%. Using this process, all of the etheral substituted monosaccharides of the present invention were prepared.

The compounds of the present invention are useful for treating animals and mammals with inflammatory and/or autoimmune disorders such as psoriasis, atopic dermatitis, rheumatoid arthritis, osteoarthritis, scleroderma and systematic lupus erythematosus.

Due to their valuable pharmacological properties, the monosaccharide compounds of the present invention or their physiologically acceptable acid-addition salts are particularly suitable for use as active compounds in pharmaceutical compositions for the treatment of, for example, inflammatory rheumatic disorders. The compounds can either be administered alone in the form of microcapsules, in mixtures with one another or in combination with acceptable pharmaceutical carriers.

The invention thus also relates to pharmaceutical compositions which comprise an effective amount of at least one compound of the present invention, if appropriate, in the form of an acid-addition salt, with or without a pharmaceutically and physiologically acceptable carrier Also provided is a method of treating animals or humans suffering from inflammatory and/or autoimmune disorders which comprises administering thereto an effective amount of at least one of the compounds of the invention or an acid-addition salt thereof, with or without a pharmaceutically acceptable carrier.

The compositions according to the invention can be administered orally, topically, rectally, internasally, or, if desired, parenterally; oral administration is preferred.

Suitable solid or liquid galenic formulations are, for example, granules, powders, coated tablets, microcapsules, suppositories, syrups, elixirs, suspensions, emulsions, drops or injectable solutions, and also preparations having a protracted release of the active compound, in the production of which adjuvants, such as excipients, disintegrants, binders, coating agents, swelling agents, glidants, or lubricants, flavors, sweeteners or solubilizers are usually used. Frequently used adjuvants which may be mentioned are, for example, magnesium carbonate, titanium dioxide, lactose, mannitol and other sugars, talc, lactalbumin, gelatin, starch, cellulose and its derivatives, animal and vegetable oils, polyethylene glycols and solvents, such as, for example, sterile water and monohydric or polyhydric alcohols, for example, glycerol.

The pharmaceutical compositions are preferably produced and administered in dosage units, each unit containing as active component a certain dose of at least one compound of the present invention and/or at least one of its physiologically acceptable acid-addition salts In the case of animals or humans, the dose can range from about 1 to 100 mg per kilogram of body weight per day, preferably 10–100 mg. In the case of in vitro testing, the effective amount to achieve a 50% inhibition of the cultured cells range from about 1–100 $\mu$g/ml of culture medium, preferably 10–100 $\mu$g.

The following examples are to be considered as illustrative only, and are not to be considered as limitative in any manner of the claims which follow. In these examples, NMR were recorded on a Varian XL-300 MHz using TMS as the internal standard reference, FTIR spectra were recorded on a Perkin-Elmer 1600 instrument using KBr plates and optical rotation was measured on a Perkin-Elmer model 241 polarimeter.

EXAMPLE 1

1,2-O-isopropylidene-6-O-trimethylacetyl-$\alpha$,D-glucofuranose

To a stirred solution of 1,2-O-isopropylidene-$\alpha$,D-glucofuranose (i.e., 220 g, 1.0 mole) in dry $CH_2Cl_2$ (300 ml) was added dry pyridine (300 ml). Trimethylacetyl chloride (120.5 g, 1 mole) was then added dropwise, with stirring at room temperature, over a period of 30 minutes until all the trimethylacetyl chloride had been added. A GC analysis showed the complete disappearance of the starting material. Dichloromethane was removed with rotary evaporation and then subjected to high vacuum to remove pyridine. Water (300 ml) was added to the reaction flask and the solid formed was filtered, washed with water and dried. It was then recrystallized from methanol. The yield of the pure product was 290 g (95.39%) m.p. 151°-151.7° C.

NMR ($CDCl_3$): $\alpha$5.99 (d, 1H, $H_1$), 4.58 (d, 1H, $H_2$), 4.44 (m, 1H, $H_4$), 4.39 (m, 1H, $H_3$), 4.25 (m, 2H,$H_6$), 4.10 (m, 1H,$H_5$), 3.13 (d 1H,OH) 3.06 (d, iH,OH), 1.50 (S, 3H, $CH_3$), 1.34 (s, 3H,$\overline{CH_3}$), 1.25 (s, 9H, —$\overline{C}(CH_3)_3$.

CIMS: 322 (M+18). $\overline{6}$26 (Dimer+18).

EXAMPLE 2

1,2:3,5-Di-O-isopropylidene-6-O-(trimethylacetyl)-$\alpha$,D-glucofuranose

A mixture of 1,2-O-isopropylidene-6-O-trimethylacetyl-$\alpha$,D-glucofuranose (144 g, 0.473 moles), dimethoxypropane (400 ml) and a catalytic amount of p-toluene sulfonic acid (4 g) was refluxed for 30 minutes. (The progress of the reactions was followed by TLC and GC.) After the reaction was complete, the flask was cooled and the excess of dimethoxypropane was removed under rotary evaporator. The residue so formed was dissolved in $CH_2Cl_2$ (250 ml), washed with saturated $NaHCO_3$ solution (3×50 ml), and brine (2×25 ml). The organic layer was dried (anhydrous $MgSO_4$) and the solvent removed. The product showed a single homogeneous spot on TLC and was used as such for the next step without further purification. Yield of the colorless oil was 154 g (94.5%).

NMR ($CDCl_3$): $\sigma$5.99 (d, 1H), 4.65 (d, 1H), 4.30 (m, 1H), 4.16 (m, 1H), 3.77 (m, 1H), 1.486 (S. 3H), 1.353 (S, 3H), 1.339 (S, 3H), 1.331 (S, 3H), 1.206 (S, 9H).

CIMS: 345 (M+1), 362 (M+18).

EXAMPLE 3

1,2:3,5-Di-O-isopropylidene-$\alpha$,D-glucofuranose ($DGF_1$)

1,2:3,5-Di-O-isopropylidene-6-O(trimethylacetyl)-$\alpha$,D-glucofuranose (125 g, 0.366 moles) was suspended in aqueous sodium hydroxide solution (126 g NaOH dissolved in 500 ml of distilled water) and the mixture refluxed, with ample stirring, for 40 min. (The progress of the reaction was monitored by GC and TLC.) After the completion of the reaction, the reaction mixture was cooled and extracted with dichloromethane (4×200 ml), washed with cold water (3×50 ml), organic layer dried ($MgSO_4$) and the solvent removed. The colorless viscous oil so formed showed a single homogeneous spot on the TLC. Upon standing the compound crystallized to a white solid having a melting point of 96.5° to 97.2° C. The yield of the product was 95 g (100%).

[$\alpha$]at 25°: D spectral line of sodium= +51.8° in methanol.

IR (neat): 3475 $Cm^{-1}$(broad OH).

CIMS: 261 (M+1), 278 (M+18).

NMR ($CDCl_3$): $\sigma$6.01 (d. 1H, $H_1$), 4.60 (m, 1H$_2$), 4.37 (m, 1H,$H_4$), 4.20 (d, 1H,$H_3$), 3.86 (m, 1H,$H_6$), 3.65 (m, 2H, $\overline{CH_2}$—OH), 1.92 (bs, 1H,OH, $D_2O$ exchangeable), 1.50 (s, 3H), 1.37 (S, 6H), 1.34 ($\overline{S}$, 3H).

EXAMPLE 4

1,2:3,5-Di-O-isopropylidene-6-deoxy-6-S-3'(N',N-dimethylaminopropyl)-$\alpha$-D-glucofuranose Step 1

1,2:3,5-Di-O-isopropylidene-6-O-tosyl-$\alpha$,D-glucofuranose

To a solution of $DGF_1$ (24 g, 0.092 moles) in pyridine (100 ml) was added a solution of p-toluene sulfonyl chloride (22.5 g, 0.118 moles) in pyridine (50 ml) with stirring at a temperature of 5°–10° C., over a period of 10 minutes slowly, the reaction temperature was raised to room temperature and stirred for a period of 3 hours (the progress of the reaction was monitored by TLC and GC). Pyridine was then removed under high vacuum. The residue was dissolved in methylene chloride (200 ml), washed with saturated sodium bicarbonate (2×30 ml), brine (2×30 ml) and the organic layer dried (MgSO$_4$). The residue obtained was dissolved in minimum amount of ethanol (30 ml) and 200 ml cold water was added. Solid so obtained, after scratching, was filtered, washed with water and then with hexane to remove the yellow coloration. The yield of the pure product was 85%, MP 72.3°–72–6° C.,

CIMS 432 (M+18).

Step 2

2:3,5-Di-O-isopropylidene-6-deoxy-6-bromo-α,D-glucofuranose

Lithium bromide (3.48 g; 0.04 moles) was added to a solution of DGF$_1$—OTs (8.28 g, 0.02 moles) in anhydrous dimethylformamide (50 ml) and the mixture stirred at 80°–90° C. for 8 hours. DMF was removed under diminished pressure and CH$_2$Cl$_2$ (100 ml) was added to the remaining residue. Solid formed was filtered and washed with dichloromethane and was washed with brine (2×25 ml), the organic layer was dried and solvent was removed. The product was purified by flash chromatography using ether:hexane (50:50) to yield: 80.2% of clear viscous oil

CIMS: 340/342 (M+18).

Step 3

1,2:3,5-Di-O-isopropylidene-6-deoxy-6-thio-α,D-glucofuranose 6-deoxy-6-bromo-DGF$_1$ (1 g) was dissolved in methanol (20 ml) and added to solid sodium hydrosulfide (1 g). The reaction mixture was refluxed for 3 hours (the progress of the reaction was followed by TLC and GC). Methanol was then removed and the residue was dissolved in CH$_2$Cl$_2$ (50 ml), washed with water (3×50 ml) brine (1×10 ml) and the solvent removed. A colorless viscous oil so obtained (0.75 g) was pure and showed a single homogeneous spot on TLC and single peak on GC.

CIMS: 277 (M+1) 294 (M+18).

Step 4

1,2:3,5-Di-O-isopropylidene-6-deoxy-6-S-3′(N′,N′-dimethylaminopropyl)-α,D-glucofuranose A mixture of 6-deoxy-6-thio-DGF$_1$ (5 g, 0.018 moles) and solid sodium hydroxide (2.7 g) was mixed together and heated under diminished pressure (0.1 mm Hg) at 100° C. for 30 minutes. The vacuum line was then disconnected and N′,N′-dimethylaminopropyl chloride (3.30 g; 0.027 moles was added, mixed and heated at the same temperature for 1 hour. The flask was then cooled and the residue was dissolved in dichloromethane (50 ml), filtered through Celite, washed with dichloromethane (50 ml) and the solvent removed. The product obtained was subjected to flash chromatography using Et$_2$O:Hexane =60:40.

The yield of the pure product was 6.0 g (92%).

NMR (CDCl$_3$): σ5.99 (d, 1H, H$_1$), 4.57 (d, 1H, H$_2$), 4.35 (m, 1H, H$_4$), 4.21 (d, 1H, H$_3$), 2.35 (t, 2H, NCH$_2$), 1.75 (quin, 2H, N—CH$_2$—CH$_2$), 3.53 (t, 2H,O-C$\overline{H}$$_2$), 1.49 (s, 3H), 1.37 (s, 3H), 1.36 (s, 3H), 1.32 (s, 3H).

CIMS: 346 (M+1).

EXAMPLE 5

1,2-O-isopropylidene-3-O-(n-heptyl)-α,D-glucofuranose (a) 1,2:5,6-Di-O-isopropylidene-3-O-(n-heptyl)-α,D-glucofuranose 1,2:5,6-Di-O-isopropylidene-α,D-glucofuranose (DGF) (10 g; 0.038 moles) and dry powdered sodium hydroxide (5.76 g) were blended together and heated at 140° C. under vacuum (1 mm Hg) for a period of 30 minutes with continuous stirring. Sodium salt of DGF so formed was cooled to 120° C. and the vacuum line was disconnected. 1-bromoheptane (10.32 g; 0.257 moles) was added in the reaction flask and stirred for 1 hour at 120° C. (The progress of the reaction was monitored by TLC). After completion of the reaction, the flask was cooled to ambient temperature and the residue was dissolved in methylene chloride (100 ml), filtered, washed with CH$_2$Cl$_2$ (50 ml) and the solvent removed. The crude mixture so obtained was purified by flash chromatography using Ether:Hexane=70:30. The yield of the pure product was 12 g (86.9%).

NMR (CDCl$_3$): σ5.87 (d, 1H,H$_1$), 1.55 (t, 2H, CH$_2$O), 0.88 (t, 3H, CH$_2$CH$_3$).

CIMS: 358 (M+1).

(b) 1,2-O-isopropylidene-3-O-(n-heptyl)-α,D-glucofuranose 1,2:5,6-Di-O-isopropylidene-3-O-(n-heptyl)-α,D-glucofuranose (2.86 g, 7.9 moles) was dissolved in tetrahydrofuran (6 ml). The flask was cooled at 5° C. To this stirred solution was added an ice cold solution of 30% perchloric acid (6 ml) and the mixture stirred for another 38 minutes. (The progress of the reaction was followed by TLC) After the completion of the reaction, a saturated solution of potassium carbonate was added until pH 10 was achieved. The reaction mixture was then filtered through Celite, washed with THF and solvents removed under diminished pressure. The product was purified by flash chromatography using 70:30 Et$_2$O: Hexane. The yield of the pure product was 99%.

NMR (CDCl$_3$): σ5.93 (d, 1H), 4.58 (d, 1H), 2.55 (t, 2H), 0.89 (t, 3H).

CIMS: 319 (M+1).

EXAMPLE 6

1,2-O-isopropylidene-3-deoxy-3-amino-3′-(propana-1′-ol)-α,D)-allofuranose (a) 1,2:5,6-Di-O-isopropylidene-3-deoxy-3-amino-3′-(propan-1′-ol)-α,D-allofuranose 1,2:5,6-Di-O-isopropylidene-α,D-ribo-hexofuranose-3-ulose [prepared by the procedure reported in Methods in Carbohydrate Chemistry, Volume VI, p 125. ] (5.16 g, 0 02 moles) was dissolved in 100 ml of methanol. To this was added 4A Molecular Sieves (3 g) and 1-amino-propanol (3 g; 0.04 moles) while stirring. The reaction mixture was stirred at room temperature, under N$_2$, for 12 hours and then the flask was cooled to about 5°–10° C. and sodium borohydride (1.52 g) was added. The mixture was stirred another 30 minutes. The excess NaBH$_4$ was decomposed by adding 5 ml of acetone and the solution filtered through Celite, washed with methanol (50 ml) and the solvent removed. The product was purified by column chromatography using 100% Et$_2$O. The yield of the pure product was 78%. NMR (CDCl$_3$): σ5.78 (d, 1H), 4.65 (t, 1H), 3.08 (m, 2H), 2.76 (m, 2H), 1.72 (m, 2H), 1.51 (s, 3H), 1.43 (s, 3H), 1.34 (s, 3H), 1.33 (s, 3H).
CIMS: 318 (M+1).

(b) 1,2-O-isopropylidene-3 deoxy-3-amino-3'-(propan-1'-ol)-α,D-allofuranose

A solution of 1,2:5,6-Di-O-isopropylidene-3-deoxy-3-amino-3'-(propan-1'-ol)-α,D-allofuranose (1 g, 3.15 mmol) was dissolved in THF (1 ml) and cooled to 5° C. Concentrated hydrochloric acid (0.5M, 1 ml) was added in one portion. The mixture was stirred at this temperature for 45 minutes (followed by TLC). After the completion of the reaction, a saturated solution of K$_2$CO$_3$ was added until pH 10 was achieved. The reaction mixture was then filtered through Celite, washed with THF and solvents removed under diminished pressure. The yield of the pure product, obtained after purification by column chromatography using ET$_2$O: CH$_3$OH=90:10, was 85%.

NMR (CDCl$_3$): σ5.78 (d, 1H,H$_1$), 4.73 (t, 1H, H$_2$), 1.75 (m, 2H), 1.55 (s, 3H), 1.37 (s, 3H).
CIMS: 278 (M+1).

EXAMPLE 7

1,2:3,5 Di-O-isopropylidene-6-O-2'(N'-ethyl pyrrolidyl)-α,D-glucofuranose

A mixture of 1,2:3,5-Di-O-isopropylidene-α,D-glucofuranose (DGF$_1$), (30 g, 0.115 moles) and dry powdered sodium hydroxide (17.28 g) was mixed together and heated at 100° C. under vacuum (0.1 mm Hg) for 90 minutes with continuous mechanical stirring. The vacuum line was then disconnected and 1-(2-chloroethyl) pyrrolidine (23.10 g; 0.173 moles) was added in one portion and the mixture stirred at 110° C. for 40 minutes. After completion of the reaction (followed by TLC and GC), the flask was cooled to ambient temperature and the residue was dissolved in dichloromethane (100 ml), filtered through Celite, washed with CH$_2$Cl$_2$ (50 ml) and the solvent removed. The pure product was obtained in 89% yield after purification by flash chromatography. (Et$_2$O: Hexane=80:20). NMR (CDCl$_3$): σ5.99 (d, 1H, H$_3$), 2.69 (t, 2H, N—CH$_2$), 2.54 (bm, 4H, ring protons), 1.76 (bm, 4H ring protons).
CIMS: 358 (M+1).

An assay was conducted to demonstrate the ability of the compounds of the present invention to modulate T-lymphocyte activity. It is known that the induction and maintenance of most inflammatory diseases are typically due to the unrestricted activity of T-lymphocytes. Therefore, it is advantageous to identify compounds which are modulators of T-lymphocyte activity for eventual use in the regulation of inflammatory diseases, including psoriasis, systemic lupus, erythematosus, and rheumatoid arthritis.

A simple method which is used to screen compounds for their ability to modulate T-lymphocyte activity comprises assessing the capacity of the compounds to alter the activation of murine spleen cells in response to T-lymphocyte activators, such as concanavalin-A (Con-A). The method used to measure the effects of the compounds of the present on the blastogenic response of spleen cells to the T-lymphocyte mitogen, (i.e., Con-A), is as follows.

The effect of the claimed compounds on the activity of mouse splenic T-lymphocytes was determined by measuring the influence of various doses of the compounds on the capacity of the spleen cells to proliferate to the T-cell mitogen, Con-A. Several different concentrations of Con-A were used to identify the effects of the compounds on the optimal and suboptimal doses of the T-lymphocyte mitogen.

Spleen cells were removed from normal C57B1/6 mice and homogenized to obtain a single cell suspension. Erythrocytes were lysed by hypotonic shock Upon determination of the viability and concentration of the remaining lymphoid cells, they were adjusted to a concentration of $4 \times 10^6$/ml. These spleen cells ($2 \times 10^5$ cells per 50μl) were seeded into wells of microtiter plates with the compounds of the present invention having the following concentrations:

Group 1: 0 μg/ml
Group 2: 10 μg/ml
Group 3: 100 μg/ml
Group 4: 200 μg/ml
Group 5: 1,000 μg/ml Con-A was also added to these cultures at a final concentration of 4 and 1 μg/ml. These cells were cultured for 3 days at 37° C. in a humidified atmosphere of 5% CO$_2$ in air. For the last 18 hours of culture, 1 μCi$^3$H-thymidine was added to each well. The cells were then precipitated by a multi-channel harvester. The amount of $^3$H-thymidine incorporated by the cultured cells were measured in a liquid scintillation counter (Disintegrations per min., DPM). All assays were conducted in triplicate.

The incubation medium used for the blastogenesis assays was RPMI-1640 medium containing 10% fetal bovine serum, 100 μg/ml streptomycin, 100 U/ml penicillin, 0.2M Hepes buffer solution, $5 \times 10^{-5}$M 2-mercaptoethanol and 2 mM glutamine.

The differences in the blastogenic response by splenic T-lymphocytes in the presence of the subject compounds versus the control medium (which did not contain the present compounds) can be seen from data reported in Table 1.

TABLE 1

| Compound | CoN-A μg/ml | Inhibitory Effect at Varying Concentrations | | | | | | | |
|---|---|---|---|---|---|---|---|---|---|
| | | 1,000 μg/ml | | 200 μg/ml | | 100 μg/ml | | 10 μg/ml | |
| | | DPM | Effect | DPM | Effect | DPM | Effect | DPM | Effect |
| Example 4 | 4 | 165 ± 56 | −100 | 92,923 ± 21,767 | −65 | 209,677 ± 18,554 | −21 | 271,920 ± 24,614 | +3 |
| | 1 | 402 ± 232 | −99 | 16,000 ± 4,056 | −75 | 37,637 ± 5,347 | −41 | 71,098 ± 5,677 | +11 |
| Example 5 | 4 | 601 ± 287 | −100 | 149,927 ± 12,981 | −43 | 252,047 ± 18,441 | −4 | 268,867 ± 2,292 | +2 |
| | 1 | 300 ± 75 | −100 | 25,949 ± 4,713 | −60 | 42,129 ± 7,437 | −34 | 71,242 ± 4,462 | +11 |
| Example 6 | 4 | 6,639 ± 2,277 | −98 | 191,580 ± 13,241 | −27 | 240,347 ± 18,731 | −9 | 256,293 ± 13,935 | −3 |
| | 1 | 1,148 ± 523 | −98 | 46,744 ± 2,575 | −27 | 52,414 ± 5,027 | −18 | 65,548 ± 10,414 | +2 |
| Example 7 | 4 | 883 ± 303 | −100 | 214,753 ± 20,788 | −19 | 240,847 ± 12,548 | −9 | 237,200 ± 16,556 | −10 |
| | 1 | 752 ± 389 | −99 | 41,856 ± 11,292 | −35 | 58,283 ± 8,001 | −9 | 64,306 ± 6,899 | 0 |
| THERA-FECTIN ® | 4 | 312,000 ± 9,233 | −19 | 254,073 ± 14,282 | −4 | 242,033 ± 14,061 | −8 | 234,593 ± 17,165 | −11 |
| | 1 | 24,169 ± 4,347 | −62 | 71,041 ± 7,356 | −11 | 64,452 ± 10,904 | +1 | 67,548 ± 3,021 | +5 |
| Control | 4 | 263,873 ± 22,152 | | | | | | | |

TABLE 1-continued

| Compound | CoN-A µg/ml | Inhibitory Effect at Varying Concentrations | | | | | | | |
|---|---|---|---|---|---|---|---|---|---|
| | | 1,000 µg/ml | | 200 µg/ml | | 100 µg/ml | | 10 µg/ml | |
| | | DPM | Effect | DPM | Effect | DPM | Effect | DPM | Effect |
| | 1 | 64,117 ± 1,407 | | | | | | | |

The results of Table 1 indicate that the compounds of the present invention produced dose-dependent, significant inhibitory effects upon the ability of normal, splenically derived, mouse T-cells to proliferate in response to mitogenic stimulation. There were less T-cells in treated cultures at the end of the assay in comparison to the untreated control cultures.

The compounds of this invention are approximately 5 times more potent than THERAFECTIN ® since significant inhibition was observed at 200 µg/ml, as opposed to the usual 1,000 µg/ml for THERAFECTIN ®. Since the T cell is the primary immuno-regulatory cell of the body, this effect suggests that compounds of the present invention have utility, from a therapeutic standpoint, in the treatment of a variety of autoimmune diseases.

A compound that inhibits skin cell proliferation, has the potential to be utilized as a dermatological drug used to treat various skin disorders such as psoriasis. Also, an anti-proliferative effect may well be observed with other tissues, such as those that line blood vessels, or joints, the uncontrolled proliferation of which produce disease, thereby broadening the scope of potential applications.

An assay was conducted to demonstrate inhibitory activity of the compounds of the present invention to the in vitro proliferation of human skin cells. The human skin cell fibroblast line was BUD-8, which was originally derived from the normal skin of a 56 year old white female and can now be obtained from the American Type Culture Collection.

This assay was used as a screen to demonstrate the effectiveness of the compounds of this invention in limiting skin cell proliferation. Anti-proliferative effects were measured with the use of a $^3$H-thymidine incorporation assay to monitor the extent of cellular proliferation by an established human skin cell fibroblast line. The experimental design used to measure the effects of the compounds on skin cell proliferation is an follows.

Cultured skin cells were mechanically detached from the surface of tissue culture flasks with a Teflon scraper. The cells were washed, resuspended in incubation medium, the viabilities were determined and the cells were resuspended to $2 \times 10^4$/ml. These cells were then plated at a density of $2 \times 10^4$ cells/0.1 ml into each microtiter well. To these cells, 0.1 ml of incubation medium was added containing the compounds of the present invention to yield the following final concentrations.

Group 1: 0 µg/ml
Group 2: 10 µg/ml
Group 3: 100 µg/ml
Group 4: 200 µg/ml
Group 5: 1,000 µg/ml These cultures were plated in triplicates per microtiter plate. After 2 days of culture, 1 µCi $^3$H-thymidine was added in a 50 µl volume to each culture well. Eighteen hours later, the $^3$H-thymidine-pulsed cells were precipitated and the amount of $^3$H-thymidine incorporation was counted on a liquid scintillation counter.

The BUD-8 cells were propagated by culture in 25 cm$^2$ flasks at 37° C. in an atmosphere of 5% $CO_2$ in air. At approximately 4–5 day intervals, or when confluence was reached, the cells were passaged. This was accomplished by detaching the cells with a Teflon scraper, washing and reseeding the cells at a lower density into fresh tissue culture flasks.

The incubation medium used for the skin cell line was RPMI-1640 medium containing 10% fetal bovine serum, 100 µg/ml streptomycin, 100 U/ml penicillin, 0.2M Hepes buffer solution, $5 \times 10^{-5}$M 2-mercaptoethanol and 2 mM glutamine.

The difference between the inhibitive effect on skin cells cultured in the presence of the compounds of the present invention versus the control medium alone can be seen from the results set forth in Table 2.

TABLE 2

| | Inhibitory Effect on Proliferation of BUD-8 Skin Cells | | | | | | | |
|---|---|---|---|---|---|---|---|---|
| | Inhibitory Effect at Varying Concentration | | | | | | | |
| | 1,000 µg/ml | | 200 µg/ml | | 100 µg/ml | | 10 µg/ml | |
| Compound | DPM | Effect | DPM | Effect | DPM | Effect | DPM | Effect |
| Example 4 | 2,634 ± 509 | −63 | 6,833 ± 1,261 | −5 | 7,471 ± 1,761 | +4 | 4,950 ± 386 | −31 |
| Example 5 | 1,514 ± 641 | −79 | 4,625 ± 890 | −35 | 4,355 ± 295 | −39 | 2,775 ± 827 | −61 |
| Example 6 | 4,280 ± 1,190 | −40 | 6,329 ± 2,114 | −12 | 6,399 ± 1,620 | −11 | 3,982 ± 791 | −45 |
| Example 7 | 3,930 ± 944 | −45 | 6,175 ± 1,221 | −14 | 5,451 ± 1,126 | −24 | 4,120 ± 950 | −43 |
| THERAFECTIN ® | 7,093 ± 2,577 | −1 | 8,839 ± 2,945 | +23 | 7,723 ± 2,353 | +8 | 5,269 ± 921 | −26 |
| Control | 7,167 ± 1,942 | | | | | | | |

As can be seen from Table 2, the compound of Example 11 produced an anti-proliferative effect that was statistically significant at a dose that is biologically attainable.

What is claimed is:

1. A monosaccharide compound selected from the group consisting of:
   1,2:3,5-Di-O-isopropylidene-6-deoxy-6-thio-3'(N',N'-dimethylamino-n-propyl)-α,D-glucofuranose;
   1,2-O-isopropylidene-3-O-n-heptyl-α,D-glucofuranose;
   1,2-O-isopropylidene-3-deoxy-3-amino-3'-(propan-1'-ol)-α,D-allofuranose; and
   1,2:3,5-Di-O-isopropylidene-6-O-2'-(N'-ethylpyrrolidyl)-α,D-glucofuranose.

2. A monosaccharide compound of claim 1, wherein the monosaccharide is 1,2:3,5-Di-O-isopropylidene-6-deoxy-6-thio-3'(N',N'-dimethylamino-n-propyl)-α,D-glucofuranose.

3. A monosaccharide compound of claim 1, wherein the monosaccharide is
1,2-O-isopropylidene-3-O-n-heptyl-α,D-glucofuranose.

4. A monosaccharide compound of claim 1, wherein the monosaccharide is
1,2-O-isopropylidene-3-deoxy-3-amino-3'-(propan-1'-ol)-α,D-allofuranose.

5. A monosaccharide compound of claim 1, wherein the monosaccharide is
1,2:3,5-Di-O-isopropylidene-6-O-2'(N'-ethylpyrrolidyl)-α,D-glucofuranose.

6. A pharmaceutical composition for the treatment of inflammatory and/or autoimmune disorders which comprises an effective amount of the compound of claim 2 or a physiologically acceptable acid-addition salt thereof with a pharmaceutically acceptable carrier.

7. A pharmaceutical composition for the treatment of inflammatory and/or autoimmune disorders which comprises an effective amount of the compound of claim 3 or a physiologically acceptable acid-addition salt thereof with a pharmaceutically acceptable carrier.

8. A pharmaceutical composition for the treatment of inflammatory and/or autoimmune disorders which comprises an effective amount of the compound of claim 4 or a physiologically acceptable acid-addition salt thereof with a pharmaceutically acceptable carrier.

9. A pharmaceutical composition for the treatment of inflammatory and/or autoimmune disorders which comprises an effective amount of the compound of claim 5 or a physiologically acceptable acid-addition salt thereof with a pharmaceutically acceptable carrier.

10. A pharmaceutical composition of claim 6 for the treatment of psoriasis.

11. A pharmaceutical composition of claim 7 for the treatment of psoriasis.

12. A pharmaceutical composition of claim 8 for the treatment of psoriasis.

13. A pharmaceutical composition of claim 9 for the treatment of psoriasis.

14. A method for treating an animal or human suffering from inflammatory and/or autoimmune disorders which comprises administering thereto an effective amount of the compound of claim 2 or a physiologically acceptable acid-addition salt thereof.

15. A method for treating an animal or human suffering from inflammatory and/or autoimmune disorders which comprises administering thereto an effective amount of the compound of claim 3 or a physiologically acceptable acid-addition salt thereof.

16. A method for treating an animal or human suffering from inflammatory and/or autoimmune disorders which comprises administering thereto an effective amount of the compound of claim 4 or a physiologically acceptable acid-addition salt thereof.

17. A method for treating an animal or human suffering from inflammatory and/or autoimmune disorders which comprises administering thereto an effective amount of the compound of claim 5 or a physiologically acceptable acid-addition salt thereof.

18. The method of claim 14, which further comprises administering the compound orally.

19. The method of claim 15, which further comprises administering the compound orally.

20. The method of claim 16, which further comprises administering the compound orally.

21. The method of claim 17, which further comprises administering the compound orally.

22. A method of claim 14 for treating an animal or human suffering from psoriasis.

23. A method of claim 15 for treating an animal or human suffering from psoriasis.

24. A method of claim 16 for treating an animal or human suffering from psoriasis.

25. A method of claim 17 for treating an animal or human suffering from psoriasis.

26. The method of claim 22, which further comprises administering the compound orally.

27. The method of claim 23, which further comprises administering the compound orally.

28. The method of claim 24, which further comprises administering the compound orally.

29. The method of claim 25, which further comprises administering the compound orally.

30. A process for preparing 1,2:3,5-Di-O-isopropylidene-α,D-glucofuranose which comprises:
adding 1,2-O-isopropylidene-α,D-glucofuranose to a solvent and a non-reactive organic base;
contacting the resultant mixture with trimethylacetyl chloride to form a 6-O-trimethylacetate ester of 1,2-O-isopropylidene-α-D-glucofuranose;
dissolving the trimethylacetate ester in 2,2-dimethyoxypropane in the presence of a catalytical amount of p-toulene sulfonic acid; and
removing the trimethylacetate ester by adding excess amounts of sodium hydroxide in aqueous solutions at reflux temperature.

31. A process of claim 30, wherein the solvent is dry methylene chloride.

32. A process of claim 30, wherein the non-reactive organic base is dry pyridine.

* * * * *